(12) United States Patent  
Sparks

(10) Patent No.: US 6,932,114 B2
(45) Date of Patent: Aug. 23, 2005

(54) FLUID DELIVERY SYSTEM AND METHOD

(75) Inventor: Douglas Ray Sparks, Whitmore Lake, MI (US)

(73) Assignee: Integrated Sensing Systems, Inc., Ypsilanti, MI (US)

(*) Notice: Subject to any disclaimer, the term of this patent is extended or adjusted under 35 U.S.C. 154(b) by 0 days.

(21) Appl. No.: 10/248,839

(22) Filed: Feb. 24, 2003

(65) Prior Publication Data

US 2003/0159741 A1 Aug. 28, 2003

Related U.S. Application Data

(60) Provisional application No. 60/358,360, filed on Feb. 22, 2002, and provisional application No. 60/399,572, filed on Jul. 30, 2002.

(51) Int. Cl.[7] ............................................. F15C 1/12
(52) U.S. Cl. .............................. 137/814; 604/67
(58) Field of Search ........................ 137/814; 604/65, 604/131, 247–249, 67, 246; 73/861, 352, 118.2

(56) References Cited

U.S. PATENT DOCUMENTS

| 3,910,256 A | * | 10/1975 | Clark et al. .................. 600/325 |
| 4,447,224 A | * | 5/1984 | DeCant et al. ................. 604/67 |
| 6,477,901 B1 | * | 11/2002 | Tadigadapa et al. ... 73/861.352 |

* cited by examiner

*Primary Examiner*—Kevin C. Sirmons
(74) *Attorney, Agent, or Firm*—Gary M. Hartmman; Domenica N. S. Hartman; Hartman & Hartman, PC

(57) ABSTRACT

A fluid delivery system capable of delivering a precise amount of fluid and monitor certain properties of the fluid so that the correct fluid is safely delivered to its intended destination. The system makes use of a flow sensor comprising a freestanding tube portion vibrated at a resonant frequency, wherein the resonant frequency corresponds to the density of the fluid flowing through the tube portion and the tube portion exhibits a degree of twist that varies with the mass flow rate of the fluid flowing therethrough. Movement of the tube portion is then sensed to produce a first output signal corresponding to the fluid density and a second output signal corresponding to the mass flow rate. The system is also equipped to measure elapsed time and to stop fluid flow in response to either of the first and second output signals.

30 Claims, 3 Drawing Sheets

FLUID DELIVERY SYSTEM AND METHOD

CROSS REFERENCE TO RELATED APPLICATIONS

This application claims the benefit of U.S. Provisional Application Ser. No. 60/358,360, filed Feb. 22, 2002, and U.S. Provisional Application Ser. No. 60/399,572, filed Jul. 30, 2002.

BACKGROUND OF INVENTION

1. Field of the Invention

The present invention generally relates to fluid handling devices, their uses and operation. More particularly, this invention relates to a fluid delivery system and method that utilizes a resonating tube to deliver a fluid and monitor multiple parameters of the delivered fluid.

2. Description of the Related Art

Infusion therapy generally involves the administration of a medication to a subject using intravenous (IV), subcutaneous and epidural routes. A wide variety of fluid infusion pumps have been developed over the years that are capable of delivering a precise amount of medication at a controlled rate. Such pumps include elastomeric, gravity fed, syringe, electrical and mechanical pumps. Valves and flow sensors have been incorporated into some infusion pump designs to improve dosage accuracy and to control the flow of fluids (e.g., drugs, medications, etc.) through these systems. More recently, micromachined flow sensors, valves and pumps have been developed, some of which have been used in medication and drug delivery applications.

Certain types of infusion therapies require extremely small amounts of fluids to be delivered in a very precise manner. However, the accuracy of infusion pumps typically range from about +/−15% for volumetric pumps, down to about +/−3% for syringe pumps. Coriolis mass flow sensors can provide flow rate measuring accuracies of under +/−1%. However, their high cost and general requirements for relatively high flow rates have restricted their use in the medical field.

Another aspect of fluid delivery systems, both within and outside the medical industry, is the prevention of gas bubbles from being delivered with the fluid. It is well known that trapped gas bubbles in the blood stream can lead to stroke or death. Because of this, IV infusion pump systems have widely employed gas bubble detectors that ultrasonically detect gas bubbles in a fluid prior to its delivery into the blood stream. An ultrasonic sensor of this type employs a transmitter and receiver positioned on opposite sides of a fluid-carrying duct, and detects a change in ultrasonic wave transmission if bubbles are present in the fluid flowing between the transmitter and receiver.

Yet another aspect of infusion therapy and various types of fluid delivery systems used outside the medical industry is the ability to sense if fluid blockage occurs. For this purpose, pressure sensors have typically been used to detect the increase in pressure that occurs as a result of an occlusion or blockage downstream of a pump. In IV infusion pump systems, two pressure sensors are often used, placed upstream and downstream of the infusion location, to monitor blockage.

In view of the above considerations, IV infusion pump systems have often employed four separate sensors: two pressure sensors to monitor blockage, an ultrasonic device to detect gas bubbles, and a flow sensor to measure fluid flow. It would be advantageous if the number of separate devices required to perform these functions could be reduced, while maintaining or improving the precision by which these functions are performed.

SUMMARY OF INVENTION

The present invention provides a fluid delivery system capable of delivering a precise amount of fluid, such as a fluid required for medical treatment, while also monitoring certain characteristics or properties of the fluid so that the correct fluid is safely delivered to its intended destination. In a preferred embodiment, the system makes use of a flow sensor of the type disclosed in U.S. Pat. No. 6,477,901 to Tadigadapa et al., wherein a micromachined resonating tube operates on the basis of the Coriolis effect to sense mass flow and density of a flowing fluid.

The fluid delivery system of this invention includes a fluid-handling unit that comprises a flow sensor adapted to receive a fluid from a fluid source and delivering the fluid to a desired destination, such as a tube used in infusion therapy to administer a medication. The flow sensor comprises a freestanding tube portion through which the fluid flows. The fluid-handling unit further comprises means for vibrating the freestanding tube portion at a resonant frequency thereof, wherein the resonant frequency will vary with the density of the fluid flowing therethrough. According to the known Coriolis effect, while vibrating at its resonant frequency the freestanding tube portion exhibits a degree of twist that varies with the mass flow rate of the fluid flowing therethrough. Movement of the freestanding tube portion is then sensed to produce a first output signal based on the resonant frequency of the freestanding tube portion and a second output signal based on the degree of twist of the freestanding tube portion. In order for the fluid-handling unit to meter out a desired amount of the fluid, the unit is also equipped with means for measuring the elapsed time during which the fluid has flowed through the fluid handling unit, and means for stopping the flow of the fluid through the unit in response to either of the first and second output signals from the movement-sensing means, i.e., based on the resonant frequency of the freestanding tube portion in response to variations in the fluid density and/or in response to the amount of fluid that has flowed through the unit based on the degree of twist of the freestanding tube portion over a measured elapsed time.

In view of the above, the present invention also provides a fluid delivery method that involves flowing a fluid through the freestanding tube portion while the tube portion is vibrated at resonance, such that the tube portion exhibits a degree of twist that varies with the mass flow rate of the fluid flowing therethrough. Movement of the freestanding tube portion is then sensed to produce the first output signal based on the resonant frequency of the tube portion and the second output signal based on the degree of twist of the tube portion. Flow of the fluid is then stopped in response to either of the first and second output signals, i.e., in response to variations in the fluid density and/or the amount of fluid that has flowed through the unit over a measured elapsed time.

The fluid delivery system described above is capable of delivering a precise amount of a fluid using a limited number of discrete fluid-handling devices. For example, whereas IV infusion pump systems have often employed four separate sensors to monitor blockage, detect gas bubbles, and measure fluid flow, the present invention can make use of a single fluid-handling unit that is capable of all three functions. Specifically, because mass flow rate is sensed by the vibrating tube portion, a sudden decrease in flow rate signifies the occurrence of an occlusion in the fluid-handling unit, while the knowledge of flow rate over time enables the fluid-handling unit to deliver a known quantity of fluid. In addition, the ability to detect fluid density enables the fluid-handling unit to detect the presence of a second phase, such as gas bubbles, in the fluid.

The fluid delivery system and its operation can be adapted for a variety of applications within and outside the medical industry. As noted above, if used to intravenously deliver fluids, the system is able to detect gas bubbles entrained within the fluid as a result of a change in fluid density that occurs because of the much lower density of gases. Based on the sensed fluid density, the system is also capable of detecting when the density of the fluid does not correspond to the fluid intended for delivery, indicating that the wrong fluid has been mistakenly used. Alternatively or in addition, the fluid-handling unit can be used in combination with a pump for delivering a precise amount of fluid. For example, the fluid-handling unit can be used with a balloon pump placed downstream of the unit, wherein fluid is accumulated until the unit has determined that the desired amount of fluid has flowed through the unit. A valve can then be operated to close the fluid path, after which the pump can deliver the accumulated fluid to its intended destination. The fluid-handling unit can also be used in combination with other types of pumps, such as a syringe pump in which case the fluid-handling unit is preferably placed between the pump and the intended destination for the fluid. Finally, the fluid-handling unit of this invention can be used in combination with a variety of other sensors, such as glucose sensors capable of being implanted in a patient and signaling when the system is required to deliver insulin to the patient.

Other objects and advantages of this invention will be better appreciated from the following detailed description.

DETAILED DESCRIPTION

Figure 1:
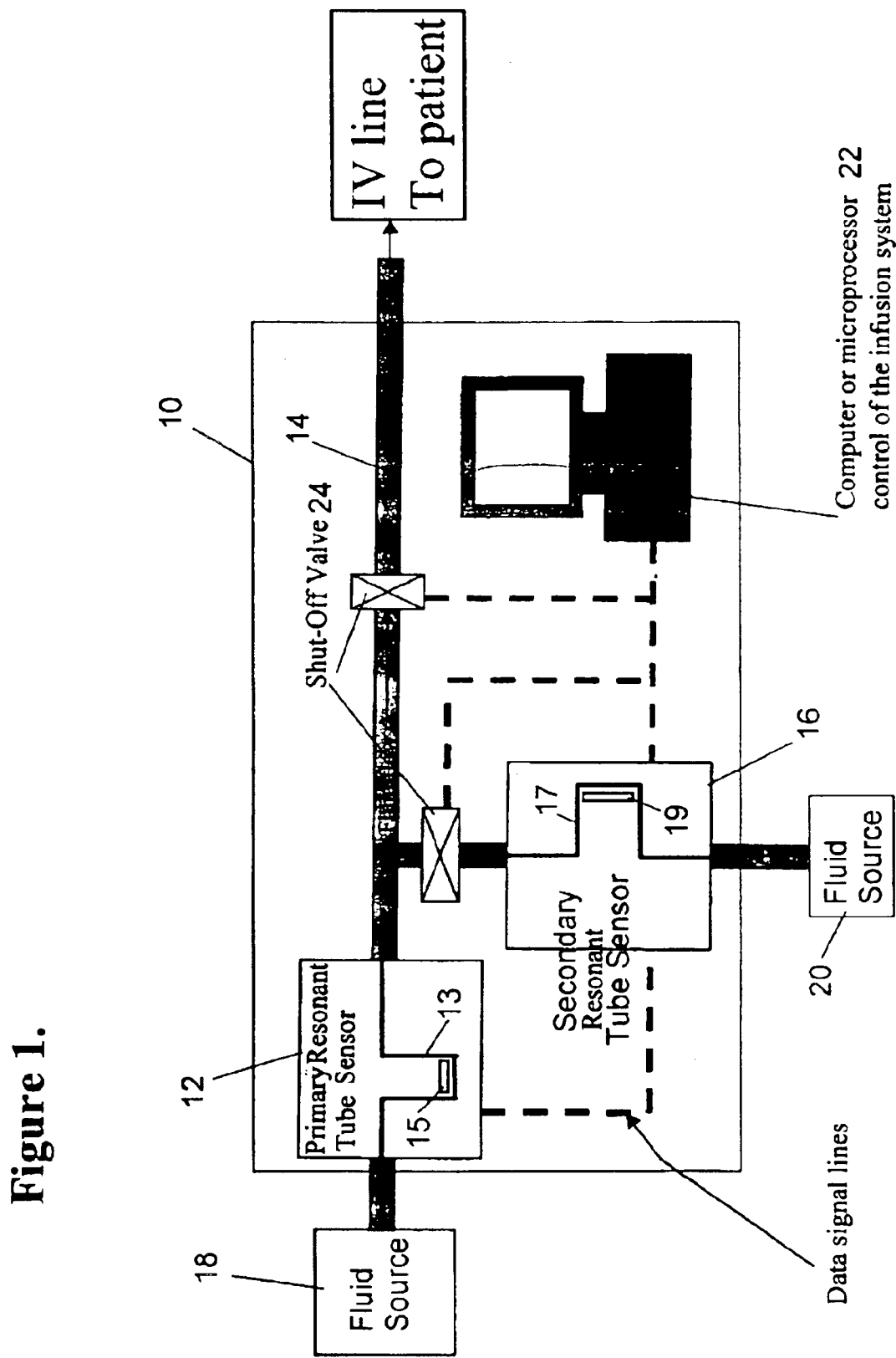
FIG. 1 is a schematic of a fluid delivery system in accordance with this invention.

With reference to FIG. 1, a fluid delivery system 10 is shown that utilizes a primary flow sensor 12 through which a fluid flows for delivery through a tube 14 to a patient, and a secondary flow sensor 16 through which a second fluid, such as a medication, flows for infusion into the primary fluid flow. The primary and secondary fluids are represented as flowing from primary and secondary fluid sources 18 and 20, respectively, to the flow sensors 12 and 16. The tube 14 may be an IV tube used to administer a medication intravenously, though the invention is also suitable for use with other methods of drug injection, such as intra-arterial, subcutaneous, intramuscular (IM), intraperitoneal (IP) and intrathecal.

According to a preferred aspect of this invention, each flow sensor 12 and 16 comprises a tube that serves as a conduit through which its respective fluid flows, with a U-shaped freestanding portion 13 and 17 of each tube being vibrated at resonance in a manner that enables certain properties of the fluid to be measured using Coriolis force principles. A preferred Coriolis-type resonating tube flow sensor is taught in U.S. Pat. No. 6,477,901 to Tadigadapa et al., incorporated herein by reference. In Tadigadapa et al., wafer bonding and silicon etching techniques are used to produce a suspended silicon tube on a wafer. The tube is vibrated at resonance such that, as fluid flows through the tube, the tube twists under the influence of the Coriolis effect. As explained in Tadigadapa et al., the degree to which the tube twists (deflects) when vibrated can be correlated to the mass flow rate of the fluid flowing through the tube on the basis of the change in the amplitude of a secondary resonant vibration mode. The density of the fluid is proportional to the natural frequency of the fluid-filled vibrating tube, such that controlling the vibration of the tube portion 13/17 to maintain a frequency at or near its resonant frequency will result in the vibration frequency changing if the density of the fluid flowing through the tube changes. As depicted in FIG. 1, the freestanding tube portions 13 and 17 are preferably U-shaped, though other shapes—both simpler and more complex—are within the scope of this invention.

The resonating tube flow sensor of Tadigadapa et al. is preferred for use with this invention, though it is foreseeable that other types of flow sensors could be employed. However, particularly advantageous aspects of the resonating tube sensor of Tadigadapa et al. include its very small size and its ability to precisely measure extremely small amounts of fluids, in contrast to prior art Coriolis-type flow sensors. Furthermore, the preferred flow sensor can attain flow rate measurement accuracies of under +/−1%, in contrast to other types of infusion pumps whose accuracies can range from about +/−15% for volumetric pumps down to +/−3% for syringe pumps. While the high cost and the high flow rate requirements for prior art Coriolis-type flow sensors have restricted their use in the drug delivery arena, the flow sensor of Tadigadapa et al. is able to sense the extremely low flow rates (e.g., less than 1 ml/hr) required by infusion therapy applications. Another advantage is that the preferred flow sensor has low power requirements as a result of using an electrostatic drive and capacitive sensing (collectively represented adjacent the tube portions 13 and 17 with reference numbers 15 and 19 in FIG. 1) to vibrate the tube portions 13 and 17 and sense the proximity (and therefore movement) of the tube portions 13 and 17, respectively. Accordingly, the flow sensor taught by Tadigadapa et al. is ideal for achieving the high accuracy, small size and low power requirements needed for drug infusion systems.

In FIG. 1, the primary and secondary flow sensors 12 and 16 communicate with a computer 22 (or microprocessor or its equivalent) so that the sensors 12 and 16 are controlled in a manner appropriate for the application. According to a preferred aspect of the invention, the flow sensors 12 and 16 operate to sense and measure fluid flow and detect fluid density in accordance with the teachings of Tadigadapa et al. Because fluid flow is a primary parameter sensed with a Coriolis-type vibrating tube sensor of this type, a sudden decrease in flow rate through one of the sensors 12 and 16 (corresponding to decreased tube deflection) would signify the occurrence of an occlusion in the system 10, while the quantitative measurement of fluid flow (correlated to tube deflection) enables the computer 22 (adapted to measure elapsed time or in communication with a device capable of measuring elapsed time) to communicate with the sensors 12 and 16 in a manner that causes the secondary flow sensor 16 to deliver an appropriate amount of the medication relative to the amount of primary fluid flowing through the primary flow sensor 12. Finally, the ability to detect fluid density enables each of the sensors 12 and 16 to detect the presence of a second phase, such as gas bubbles, in their respective fluids. In addition, the sensing of fluid density provides a secondary safety feature made possible with this invention, which is the ability to detect whether one of the fluids flowing through the sensors 12 or 16 has a density different from the fluid intended to be delivered, indicating that the wrong fluid is being delivered from the fluid source 18 or 20.

The ability of the sensors 12 and 16 to detect gas bubbles arises from the sensitivity of the sensors 12 and 16 to fluid density. Since the density of a gas bubble is much lower than that of a liquid, there is a detectable change in resonant frequency of the vibrating freestanding tube portions 13 and 17 of the sensors 12 and 16 when small bubbles pass therethrough. The sensed frequency of the resonating tube is converted to a density or specific gravity output, which in this case is used to detect a change in fluid density or specific gravity to indicate the presence of gas bubbles (or the use of a fluid having a different density than the intended fluid). The fluid delivery system 10 includes shut-off valves 24 that communicate with the computer 22 and can be immediately closed to stop the flow of fluid through the system 10, and therefore also stop fluid flow through the sensors 12 and 16. Various types of known valves could be used as the valves 24, including on-chip integrated micromachined valves capable of being integrated with the flow sensors 12 and 16. The system 10 can also be equipped with alarms sounded by the computer 22 or otherwise controlled by the computer 22 to notify personnel of conditions sensed by the sensors 12 and 16.

The efficacy of the resonating tube flow sensor of Tadigadapa et al. to detect the presence of gas bubbles in a fluid was demonstrated by intentionally injecting air bubbles into a water sample flowing through the sensor. The water sample was evaluated at a temperature of about 20° C., at which the density of water is about 0.998 g/cc while the density of air is about 0.0010 g/cc. The presence of the air bubbles in the water sample was evidenced by the measured density dropping into a range of about 0.142 g/cc to about 0.995 g/cc, with the lower density values corresponding to more air bubbles present in the two-phase fluid. The investigation showed that a resonating tube flow sensor constructed in accordance with Tadigadapa et al. is sufficiently sensitive to fluid density to be capable of detecting the presence of trapped gas bubbles in a flowing fluid. The investigation also indicated that the bubble density can be determined for a given fluid at a known temperature. In the medical field, this capability can be employed to screen for gas bubbles in IV fluids, such as saline solutions, plasma, blood, glucose, electrolytes and pharmaceutical fluids injected into the blood stream of a patient. The computer 22 can be used to establish an acceptable density range for any number of fluids, such that the sensors 12 and 16 can be calibrated for particulars fluids prior to use. Since fluid density varies with temperature, the system 10 is also preferably equipped with temperature sensors (not shown) to determine the temperatures of the fluids to increase the accuracy (improved bubble resolution) of the system 10.

The ability for the system 10 to detect the use of an incorrect fluid using the resonating tube flow sensor of Tadigadapa et al. was also demonstrated with a 50% Dextrose IV solution (density of about 1.167 g/cc at room temperature) and a 0.9% saline IV solution (density of about 1.00 g/cc at room temperature). The sensitivity of the flow sensor was sufficient to identify which of these fluids was being flowed through the sensor. Therefore, if an IV bag containing one of these solutions was mistakenly connected to the system 10 instead of the other solution, the density measurement function of the sensor (either 12 or 16) would identify this error, stop the flow of fluid and, if so equipped, trigger an electronic alarm. To properly implement this capability, the density of the desired solution (as well as any other solutions of interest) would be entered into the memory of the computer 22 (or other appropriate controller). Computer algorithms would preferably be used to interpret the density output signals of the sensors 12 and 16 in order to indicate whether the condition is the result of bubbles, a zero flow rate (from an occlusion), or the wrong IV solution. These algorithms could be used to gather data from the resonant flow sensors 12 and 16 to make flow/no-flow decisions and issue warnings or stop fluid flow.

Figure 2:
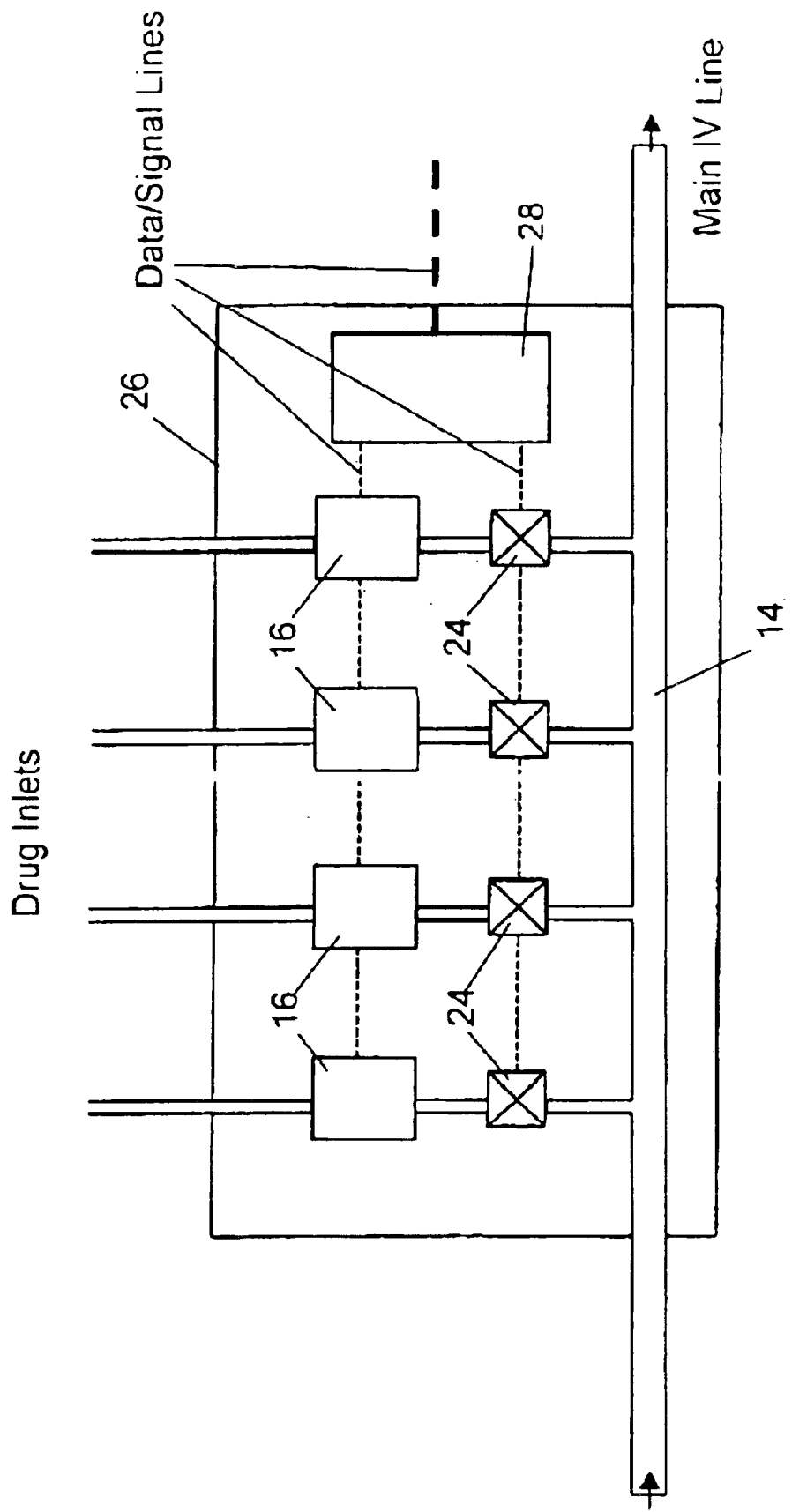
FIG. 2 is a schematic of an alternative fluid handling unit for the fluid delivery system of FIG. 1.

In view of the above, the fluid delivery system 10 depicted in FIG. 1 can provide an improved infusion pump system to detect trapped gas bubbles in an intravenous fluid that, if delivered to the blood stream, could lead to stroke or death. The fluid delivery system 10 of this invention is an improvement over prior art systems in that each of the sensors 12 and 16 is able to perform three important functions: measure fluid flow, detect blockage, and detect the presence of gas bubbles in the fluid. FIG. 2 represents a modification to the system 10 of FIG. 1, in which multiple secondary flow sensors 16 of the type represented in FIG. 1 are incorporated into a manifold infusion unit 26, such that greater quantities of a single drug or more than one drug can be injected into the common IV line 14. In FIG. 1, where the fluid delivery system 10 is shown as delivering two fluids, a total of two flow sensors 12 and 16 are used to measure fluid flow, detect blockage, and detect the presence of gas bubbles, instead of the eight sensors that would be required to perform these same tasks in accordance with prior art delivery systems. With the manifold infusion unit 26 shown in FIG. 2, flow through any one of the secondary flow sensors 16 can be independently stopped through the operation of its associated shut-off valve 24 and a dedicated electronic control circuitry 28.

Figure 3:
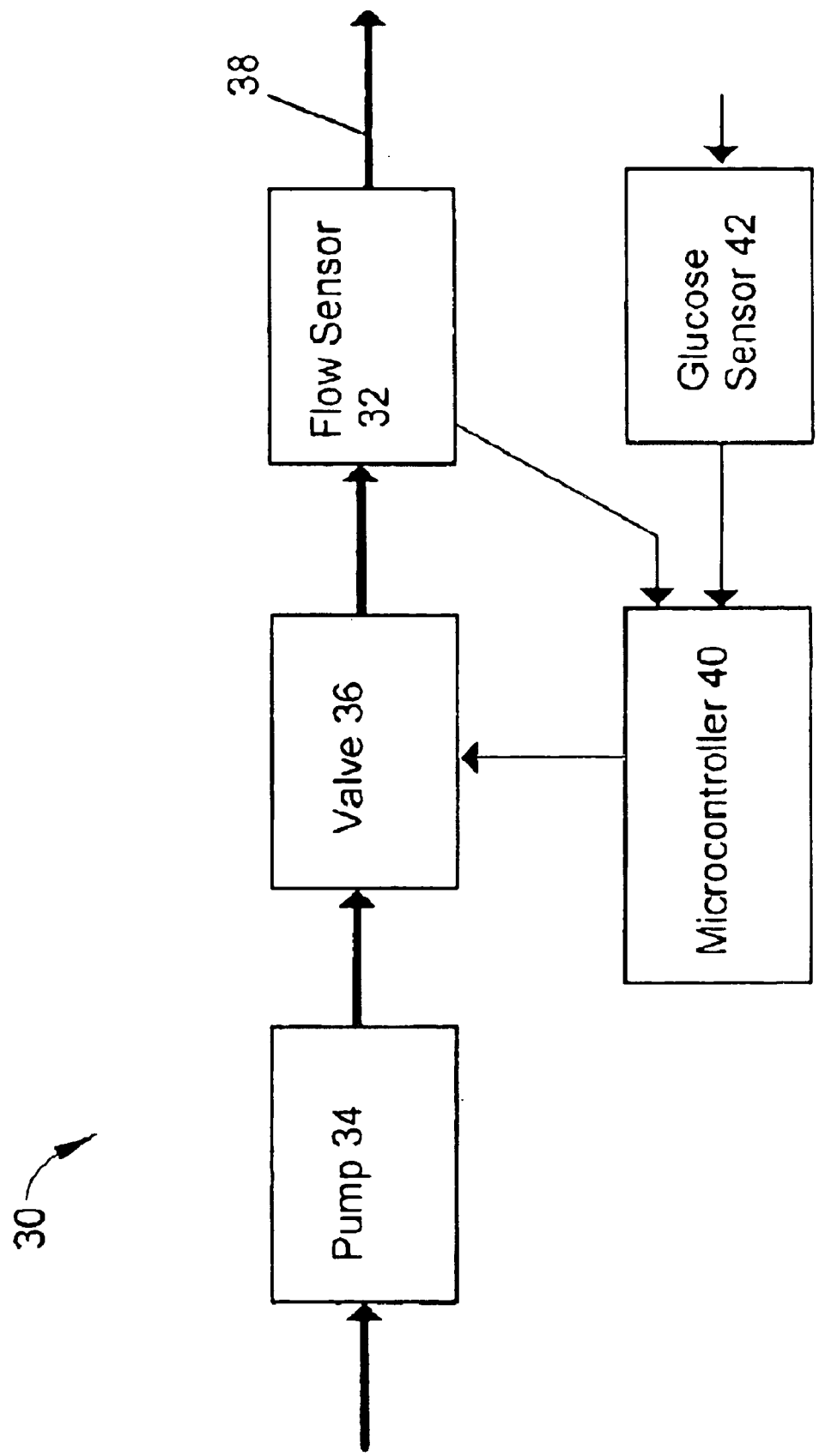
FIG. 3 is a schematic of a pumping system suitable for use with the fluid delivery system of FIG. 1.

Finally, FIG. 3 represents an embodiment of the invention by which a resonating tube flow sensor 32 of a type essentially identical to the sensor 12 of FIG. 1 can be coupled with a pump to provide an improved infusion pumping system 30. The pumping system 30 can be used independently or with the fluid delivery system 10 of FIGS. 1 and 2, which if the latter the flow sensor 32 of FIG. 3 can be substituted for the flow sensor 12 of FIG. 1. This embodiment makes use of a pump 34 and valve 36 to provide a highly accurate, low cost infusion pump that can be used alone or with the fluid delivery system 10 of FIG. 1. The mass flow of the drug to be infused through a fluid line 38 is measured by the flow sensor 32, which is depicted in FIG. 3 as receiving the fluid from the pump 34 through the valve 36. The pump 34 can be an elastomeric (balloon) pump that provides a reservoir for the fluid delivered to the sensor 32. Various other types of pumps could be used, such as a pressurized container and other relatively low cost pumps whose lower accuracy would otherwise exclude their use in the medical applications contemplated by the present invention. Once the sensor 32 indicates that the correct dose has passed therethrough, the valve 36 is operated to close the fluid line 38 upstream of the sensor 32, thereby preventing any additional flow of the fluid through the fluid line 38 to its intended destination.

In a preferred embodiment, the pumping system 30 operates with minimal power requirements. For example, the pump 34 is only operated while the desired dosage is being measured by the sensor 32, and the valve 36 is normally closed so that power is not required by the valve 36 to maintain the valve 36 closed one the desired amount of fluid has been delivered through the sensor 32. A microcontroller 40 is provided for receiving flow data from the sensor 32 and actuating the valve 36. A notable feature of this aspect of the invention is that the infusion pumping system 30 can be implanted, strapped to the body (ambulatory), or used as a stationary, bedside device.

The system 30 depicted in FIG. 3 can be modified in various ways. For example, while a timed or preprogrammed dose approach can be taken with the invention, the pumping system 30 can be coupled with other sensors to control the timing and amount of medicine dispensed. A notable example is that a glucose sensor 42 could be used to monitor the glucose level of a patient's blood to control the delivery of insulin in response to an increase or decrease in glucose level relative to preset limits. Again, the flow sensor 32 is employed to accurately monitor the dosage, while inputs from the glucose sensor 42 and flow sensor 32 could be used to determine when the valve 36 should be turned off to stop insulin flow. The system 30 can be implanted to treat diabetes, with only the insulin reservoir being external (and preferably disposable). A similar type of system 30 could be used to dispense medication for the treatment of cancer, pain, etc.

The sensor 32 and valve 36 can also be used in combination with a syringe pump (in place of the balloon pump 34 in FIG. 3), with which medication delivery rates are typically monitored by controlling the plunger motion. In the past, low-dose syringe pumps have required small syringe barrels to achieve a desired level of accuracy. A downside to this requirement is that the total volume that can be pumped accurately with a syringe pump is limited. An improved syringe pump is obtained with this invention by using a Coriolis-type flow sensor essentially identical to those described above. By inserting the sensor between the syringe and the fluid outlet, a large syringe barrel can be employed while still maintaining high accuracy of small drug volumes. Fluid output is thereby controlled based on the output of the flow sensor, instead of the position of the plunger.

While the Coriolis-type flow sensor of Tadigadapa et al. has particular features that make it preferred for use with this application, other types of flow sensors could be used. For example, with certain limitations, hot-wire, thin-film, and drag force flow sensors could be employed in the fluid delivery system 10 of this invention, as well as the embodiments of FIGS. 2 and 3. Therefore, while the invention has been described in terms of certain embodiments, it is apparent that other forms could be adopted by one skilled in the art. For example, this invention can be implemented with a vibrating tube made from various materials, including metal, glass, ceramic, silicon, semiconductor, plastic, or another rigid material, and tubes of various shapes could be used, such as U, S, Z, and L-shaped tubes, bridges, hollow cantilevers, hollow disks/diaphragms, etc. Furthermore, in addition to the intravenous medical treatment of patients discussed above, the invention can be used to deliver fluids and detect unwanted gas bubbles in fluids for a wide array of applications, such as industrial processing, chemical analysis, beverage production, deep-sea operations, etc. Therefore, the scope of the invention is to be limited only by the following claims.

What is claimed is:

1. A fluid delivery system having a fluid-handling unit comprising:
    a tube adapted for receiving a fluid from a fluid source, the tube comprising a freestanding tube portion through which the fluid flows;
    means for vibrating the freestanding tube portion of the tube at a resonant frequency thereof that varies with the density of the fluid flowing therethrough, the Coriolis effect causing the freestanding tube portion to twist while being vibrated at resonance, the freestanding tube portion exhibiting a degree of twist that varies with the mass flow rate of the fluid flowing therethrough;
    means for sensing movement of the freestanding tube portion of the tube, the movement-sensing means producing a first output signal based on the resonant frequency of the freestanding tube portion and a second output signal based on the degree of twist of the freestanding tube portion;
    means for setting a range for the first output signal corresponding to a range for the density of the fluid; and
    means for stopping flow of the fluid through the fluid handling unit in response to the first output signal from the movement-sensing means, wherein the flow-stopping means, the movement-sensing means, and the range-setting means cooperate to stop the flow of the fluid through the fluid handling unit if the density of the fluid is outside the range therefor set with the range-setting means.

2. The fluid delivery system according to claim 1, wherein the flow-stopping means stops the flow of the fluid if, based on the first output signal, the density of the fluid is outside the range therefor because the fluid contains bubbles.

3. The fluid delivery system according to claim 1, further comprising means for sounding an alarm if, based on the first output signal, the density of the fluid is outside the range therefor set with the range-setting means.

4. The fluid delivery system according to claim 1, further comprising at least a second flow sensor through which a second fluid flows, and means for stopping flow of the second fluid through the second flow sensor.

5. The fluid delivery system according to claim 1, further comprising a pumping means for delivering the fluid to the fluid handling unit, a flow sensor between the pumping means and the fluid handling unit, and a valve between the pumping means and the flow sensor, the flow sensor comprising:
    a second freestanding tube portion through which the fluid flows after being received from the pumping means;
    means for vibrating the second freestanding tube portion at a resonant frequency thereof that varies with the density of the fluid flowing therethrough; the Coriolis effect causing the second freestanding tube portion to twist while being vibrated at resonance, the second freestanding tube portion exhibiting a degree of twist that varies with the mass flow rate of the fluid flowing therethrough;
    means for sensing movement of the second freestanding tube portion, the movement-sensing means producing a first output signal based on the resonant frequency of the second freestanding tube portion and a second output signal based on the degree of twist of the second freestanding tube portion;
    means for measuring elapsed time during which the fluid has flowed through the flow sensor; and
    means for stopping flow of the fluid through the flow sensor in response to either of the first and second output signals from the movement-sensing means of the flow sensor.

6. The fluid delivery system according to claim 5, wherein the pumping means serves as a reservoir for the fluid prior to the pumping means delivering the fluid to the flow sensor.

7. The fluid delivery system according to claim 5, wherein the fluid passage is a tube for intravenous, intra-arterial, subcutaneous, intramuscular, intraperitoneal or intrathecal delivery of the fluid.

8. The fluid delivery system according to claim 1, wherein the flow-stopping means is a valve.

9. The fluid delivery system according to claim 1, wherein the fluid deliver system comprises a plurality of the fluid handling units arranged in fluidic parallel to deliver at least the fluid to a fluid passage.

10. The fluid delivery system according to claim 9, wherein at least one of the fluid handling units delivers a different second fluid to the fluid passage.

11. The fluid delivery system according to claim 1, wherein the fluid handling unit is implanted in a living subject, the fluid delivery system further comprising a sensor implanted in the living subject and in communication with the fluid handling unit for dispensing the fluid to the living subject.

12. An infusion system comprising:
a first flow sensor that receives a first fluid from a first fluid source and delivers the first fluid to a tube attached to a human subject, the first flow sensor comprising a first freestanding tube portion through which the first fluid flows, first means for vibrating the first freestanding tube portion at a resonant frequency thereof that varies with the density of the first fluid flowing therethrough, first means for sensing movement of the first freestanding tube portion, the first movement-sensing means producing a first output signal based on the resonant frequency of the first freestanding tube portion and a second output signal based on the degree of twist of the first freestanding tube portion, the Coriolis effect causing the first freestanding tube portion to twist while being vibrated at resonance, the first freestanding tube portion exhibiting a degree of twist that varies with the mass flow rate of the first fluid flowing therethrough;
a plurality of second flow sensors arranged in fluidic parallel, the second flow sensors delivering at least a second fluid from at least a second fluid source to the tube, each of the second flow sensors comprising a second freestanding tube portion through which the second fluid flows, second means for vibrating the second freestanding tube portion at a resonant frequency thereof that varies with the density of the second fluid flowing therethrough, second means for sensing movement of the second freestanding tube portion, the second movement-sensing means producing a first output signal based on the resonant frequency of the second freestanding tube portion and a second output signal based on the degree of twist of the second freestanding tube portion, the Coriolis effect causing the second freestanding tube portion to twist while being vibrated at resonance, the second freestanding tube portion exhibiting a degree of twist that varies with the mass flow rate of the second fluid flowing therethrough;
means for measuring elapsed time during which the first and second fluids have flowed through the first and second flow sensors; and
means for stopping flow of the first and second fluids through the first and second flow sensors, respectively, in response to either of the first and second output signals from the first and second movement-sensing means, wherein the flow-stopping means is operable to stop the flow of the second fluid if, based on the elapsed time determined by the time-measuring means and the second output signal of the second movement-sensing means, a specified amount of the second fluid has passed through any one or more of the second flow sensors.

13. The infusion system according to claim 12, wherein the flow-stopping means stops the flow of the second fluid if, based on the first output signal of the second flow sensor, the resonant frequency of the second freestanding tube portion is outside a range specified for the second fluid.

14. The infusion system according to claim 12, wherein the first and second movement-sensing means are effect to sense that the resonant frequencies of the first and second fluids are outside ranges specified therefor if either of the first and second fluids contains gas bubbles.

15. The infusion system according to claim 12, further comprising a pumping means for delivering the first fluid from the first fluid source to the first flow sensor.

16. The infusion system according to claim 15, wherein the pumping means serves as a reservoir for the specified amount of the fluid prior to the pumping means delivering the first fluid to the first flow sensor.

17. A fluid delivery method comprising the steps of:
flowing a fluid through a freestanding tube portion;
vibrating the freestanding tube portion at a resonant frequency thereof that varies with the density of the fluid flowing therethrough, the Coriolis effect causing the freestanding tube portion to twist while being vibrated at resonance, the freestanding tube portion exhibiting a degree of twist that varies with the mass flow rate of the fluid flowing therethrough;
sensing movement of the freestanding tube portion and producing a first output signal based on the resonant frequency of the freestanding tube portion and a second output signal based on the degree of twist of the freestanding tube portion;
measuring elapsed time during which the fluid has flowed through the freestanding tube portion; and
stopping flow of the fluid through the freestanding tube portion in response to either of the first and second output signals, wherein flow of the fluid is stopped if, based on the elapsed time and the second output signal, a specified amount of the fluid has passed through the freestanding tube portion.

18. The fluid delivery method according to claim 17, wherein flow of the fluid is stopped if, based on the first output signal, the resonant frequency is outside a range specified for the fluid.

19. The fluid delivery method according to claim 18, further comprising the step of sounding an alarm if, based on the first output signal, the resonant frequency is outside a range specified for the fluid.

20. The fluid delivery method according to claim 17, further comprising the step of delivering the specified amount of the fluid from the freestanding tube portion to a fluid passage.

21. The fluid delivery method according to claim 20, wherein a pump serves as a reservoir for the fluid prior to the pump delivering the fluid to the freestanding tube portion.

22. The fluid delivery method according to claim 20, wherein the fluid passage is a tube for intravenous, intra-arterial, subcutaneous, intramuscular, intraperitoneal or intrathecal delivery of the fluid.

23. The fluid delivery method according to claim 17, wherein a valve stops the flow of fluid.

24. The fluid delivery method according to claim 17, wherein the fluid deliver method utilizes a plurality of the freestanding tube portions arranged in fluidic parallel to deliver at least the fluid to a fluid passage.

25. The fluid delivery method according to claim 24, wherein at least one of the freestanding tube portions delivers a different second fluid to the fluid passage.

26. An infusion method comprising the steps of:

flowing a first fluid from a first fluid source through a first flow sensor to a tube attached to a human subject, the first flow sensor comprising a first freestanding tube portion through which the first fluid flows, first means for vibrating the first freestanding tube portion at a resonant frequency thereof that varies with the density of the first fluid flowing therethrough, first means for sensing movement of the first freestanding tube portion, the first movement-sensing means producing a first output signal based on the resonant frequency of the first freestanding tube portion and a second output signal based on the degree of twist of the first freestanding tube portion, the Coriolis effect causing the first freestanding tube portion to twist while being vibrated at resonance, the first freestanding tube portion exhibiting a degree of twist that vanes with the mass flow rate of the first fluid flowing therethrough;

flowing a second fluid from a second fluid source through a second flow sensor to the tube, the second flow sensor comprising a second freestanding tube portion through which the second fluid flows, second means for vibrating the second freestanding tube portion at a resonant frequency thereof that varies with the density of the second fluid flowing therethrough, second means for sensing movement of the second freestanding tube portion, the second movement-sensing means producing a first output signal based on the resonant frequency of the second freestanding tube portion and a second output signal based on the degree of twist of the second freestanding tube portion, the Coriolis effect causing the second freestanding tube portion to twist while being vibrated at resonance, the second freestanding tube portion exhibiting a degree of twist that varies with the mass flow rate of the second fluid flowing therethrough;

measuring elapsed time during which the first and second fluids have flowed through the first and second flow sensors, respectively; and stopping flow of the first and second fluids through the first and second flow sensors, respectively, in response to either of the first and second output signals from the first and second movement-sensing means, wherein the flow of the second fluid is stopped if, based on the elapsed time determined by the time-measuring means and the second output signal of the second movement-sensing means, a specified amount of the second fluid has passed through the second flow sensor.

27. The infusion method according to claim 26, wherein the flow of the second fluid is stopped if, based on the first output signal of the second flow sensor, the resonant frequency of the second freestanding tube portion is outside a range specified for the second fluid.

28. The infusion method according to claim 27, wherein the resonant frequency is outside the range specified for the second fluid as a result of the second fluid containing gas bubbles.

29. The infusion method according to claim 26, wherein a pump serves as a reservoir for delivering the first fluid from the first fluid source to the first flow sensor.

30. The infusion method according to claim 26, wherein the infusion method utilizes a plurality of the second flow sensors arranged in fluidic parallel to deliver at least the second fluid to the tube.

* * * * *